United States Patent
Sensabaugh

(10) Patent No.: US 6,991,613 B2
(45) Date of Patent: Jan. 31, 2006

(54) ANKLE FRACTURE BRACE WITH BREAK-AWAY ARM

(75) Inventor: Steve Sensabaugh, Palm Harbor, FL (US)

(73) Assignee: Restorative Care of America Incorporated, St. Petersburg, FL (US)

( * ) Notice: Subject to any disclaimer, the term of this patent is extended or adjusted under 35 U.S.C. 154(b) by 321 days.

(21) Appl. No.: 10/614,714

(22) Filed: Jul. 7, 2003

(65) Prior Publication Data

US 2005/0010151 A1 Jan. 13, 2005

(51) Int. Cl.
A61F 5/00 (2006.01)

(52) U.S. Cl. ............... 602/27; 602/23; 602/5; 602/65

(58) Field of Classification Search ............ 602/23, 602/16, 27, 5, 6, 28, 65; 36/110, 140
See application file for complete search history.

(56) References Cited

U.S. PATENT DOCUMENTS

| | | | |
|---|---|---|---|
| 2,409,195 A | | 10/1946 | Crawford |
| 2,486,687 A | * | 11/1949 | Svaetichin ............ 602/23 |
| 3,064,644 A | * | 11/1962 | Patterson ............ 602/23 |
| 4,088,129 A | * | 5/1978 | DiGiulio ............ 602/23 |
| 4,771,768 A | * | 9/1988 | Crispin ............ 602/16 |
| 4,776,326 A | * | 10/1988 | Young et al. ............ 602/16 |
| 4,962,760 A | * | 10/1990 | Jones ............ 602/27 |
| 4,974,583 A | * | 12/1990 | Freitas ............ 602/24 |
| 5,176,623 A | * | 1/1993 | Stetman et al. ............ 602/27 |
| 5,329,705 A | * | 7/1994 | Grim et al. ............ 36/88 |
| 5,464,385 A | * | 11/1995 | Grim ............ 602/27 |
| 5,605,535 A | * | 2/1997 | Lepage ............ 602/27 |
| 5,620,411 A | * | 4/1997 | Schumann et al. ............ 602/23 |
| 6,648,843 B1 | * | 11/2003 | Marciano et al. ............ 602/27 |
| 6,767,322 B1 | * | 7/2004 | Futatsugi et al. ............ 600/133 |
| 2002/0077576 A1 | * | 6/2002 | Saraceni ............ 602/27 |
| 2003/0196352 A1 | * | 10/2003 | Bledsoe et al. ............ 36/110 |
| 2004/0019307 A1 | * | 1/2004 | Grim et al. ............ 602/27 |

FOREIGN PATENT DOCUMENTS

GB  2389795 A  * 12/2003

* cited by examiner

*Primary Examiner*—Henry Bennett
*Assistant Examiner*—Shumaya B. Ali

(57) ABSTRACT

An ankle fracture brace has a foot support portion which receives a foot of a patient. A convertible leg support portion receives a leg of the patient. The leg support portion includes a pair of spaced vertical arms connected by arm lower ends to sides of the foot support portion so as to extend upwardly past sides of an ankle of a patient and terminate adjacent sides of a calf of a patient. Upper end and lower end straps secure the leg support portion to the leg of the patient. These upper end and lower end straps are connected to the vertical arms adjacent the calf and ankle, respectively. A horizontal break line is formed in each of the arms between the upper end and lower end straps permitting a user to selectively sever the arms on the break lines to accommodate different patient uses of the ankle brace.

6 Claims, 5 Drawing Sheets

ANKLE FRACTURE BRACE WITH BREAK-AWAY ARM

BACKGROUND OF THE INVENTION

Currently, lower leg braces are used for many different purposes. Conventional brace walkers are typically used for cases of post operation ankle fusions, ankle sprains, forefoot and toe-injuries, stress fractures, plantar fasciitis tears, or as a day splint walker to replace a short leg casting. These conventional brace walkers support the user's foot and extend up the user's leg to encircle a portion of his or her calf.

Low profile brace walkers (also known as low top, low profile, short leg walker, etc.) are typically used for cases of bunion surgery, metatarsal stress fractures, turf-toe-injuries, or are used in place of a post operation shoe when the patient's foot will not fit in the shoe. Since the low profile brace walkers are used for different purposes than the conventional brace walkers, the low profile brace walkers have a different overall design than the conventional brace walkers. Like the conventional brace walkers, these low profile brace walkers support the user's foot; however, they extend up the user's leg only to a position below his or her calf.

Due to the design variations between the conventional and low profile brace walkers, a supplier must necessarily manufacture and inventory both these walkers to provide products to meet the various uses desired by potential customers.

It is therefore a principle object of this invention to provide an ankle fracture brace with a leg support portion which is convertible from an original height to a shorter height.

These and other objects will be apparent to those skilled in the art.

SUMMARY OF THE INVENTION

The foregoing objects may be achieved by a convertible ankle fracture brace for immobilization and rehabilitation of the foot and ankle. The invention comprises a foot support portion which receives a foot of a patient. A convertible leg support portion receives a leg of the patient. The leg support portion includes a pair of spaced vertical arms connected by lower ends to sides of the foot support portion so as to extend upwardly past sides of an ankle of a patient and terminate adjacent sides of a calf of a patient. Upper end and lower end straps secure the leg support portion to the leg of the patient. These upper end and lower end straps are connected to the vertical arms adjacent the calf and ankle, respectively. A horizontal break line is formed in each of the arms between the upper end and lower end straps permitting a user to selectively severe the arms on the break lines to accommodate different patient uses of the ankle brace.

DESCRIPTION OF THE PREFERRED EMBODIMENT

Figure 2:
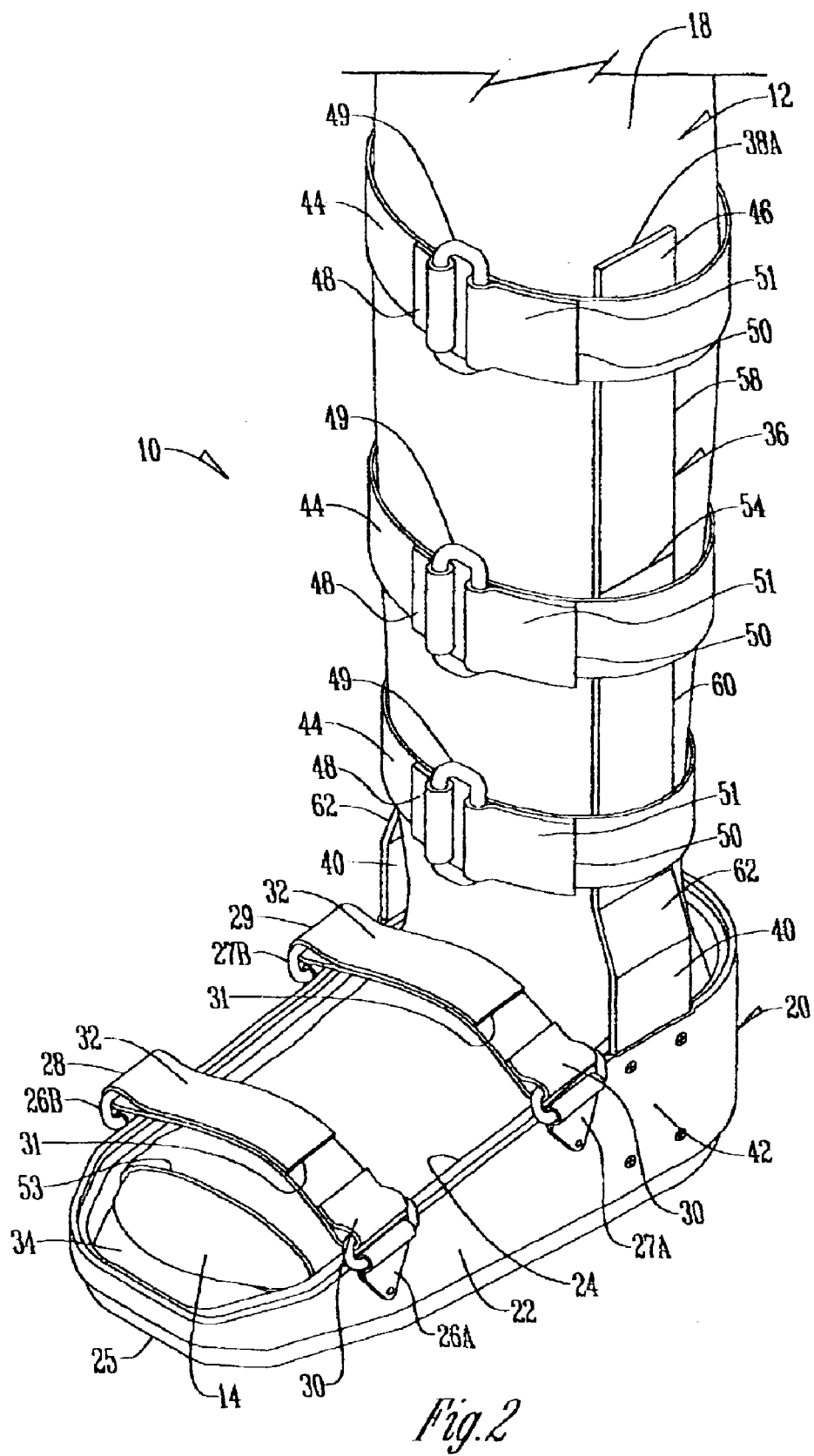
FIG. 2 is a perspective view of the ankle fracture brace of this invention similar to FIG. 1, showing the brace secured to a patients leg.

With reference to FIG. 2, the ankle fracture brace 10 of the invention is intended for the immobilization and rehabilitation of a patient's leg 12. Specifically, the brace 10 envelopes the foot 14, ankle 16, and calf 18 of a patient to immobilize the foot 14 and ankle 16.

The invention comprises a foot support portion 20 which receives the foot 14 of a patient. The foot support portion 20 has a main boot body 22 with an upper opening 24 therein for receiving the foot 14. A sole 25 is secured to the bottom of the main boot body by a layer of glue (not shown). The sole 25 is made of rubber or the like.

Two pair of strap holders 26A–B and 27A–B are connected to the main boot body 22 on opposite sides of the upper opening 24. A first foot strap 28 is removably secured between strap holders 26A–B. A second foot strap 29 is removably secured between strap holders 27A–B. The first and second foot straps 28 and 29 operate to removably secure the foot 14 within the main boot body 22.

Each of the straps 28 and 29 has a fixed loop end 30 permanently secured about respective strap holders 26A and 27A. As will be described hereafter, a plurality of Velcro® fasteners are used in this invention which include male micro hook patches which can be detachably connected to material having a plurality of female micro loops. Hook patches 31 are attached to each loose end 32 opposite of the fixed loop ends 30. Each loose end 32 is treaded through respective strap holders 26B and 27B. The first and second foot straps 28 and 29 are comprised of loop material which is adapted to be detachably secured to the hook patches 31. Thus, the straps 28 and 29 are removably secured between strap holders 26A–B and 27A–B respectively, once the hook patches 31 are detachably secured to the loop material of the first and second foot straps 28 and 29.

A foam foot pad 34 is connected to the main boot body 22 and located within upper opening 24. The foam foot pad 34 supports the foot 14 within the main boot body 22.

Figure 1:
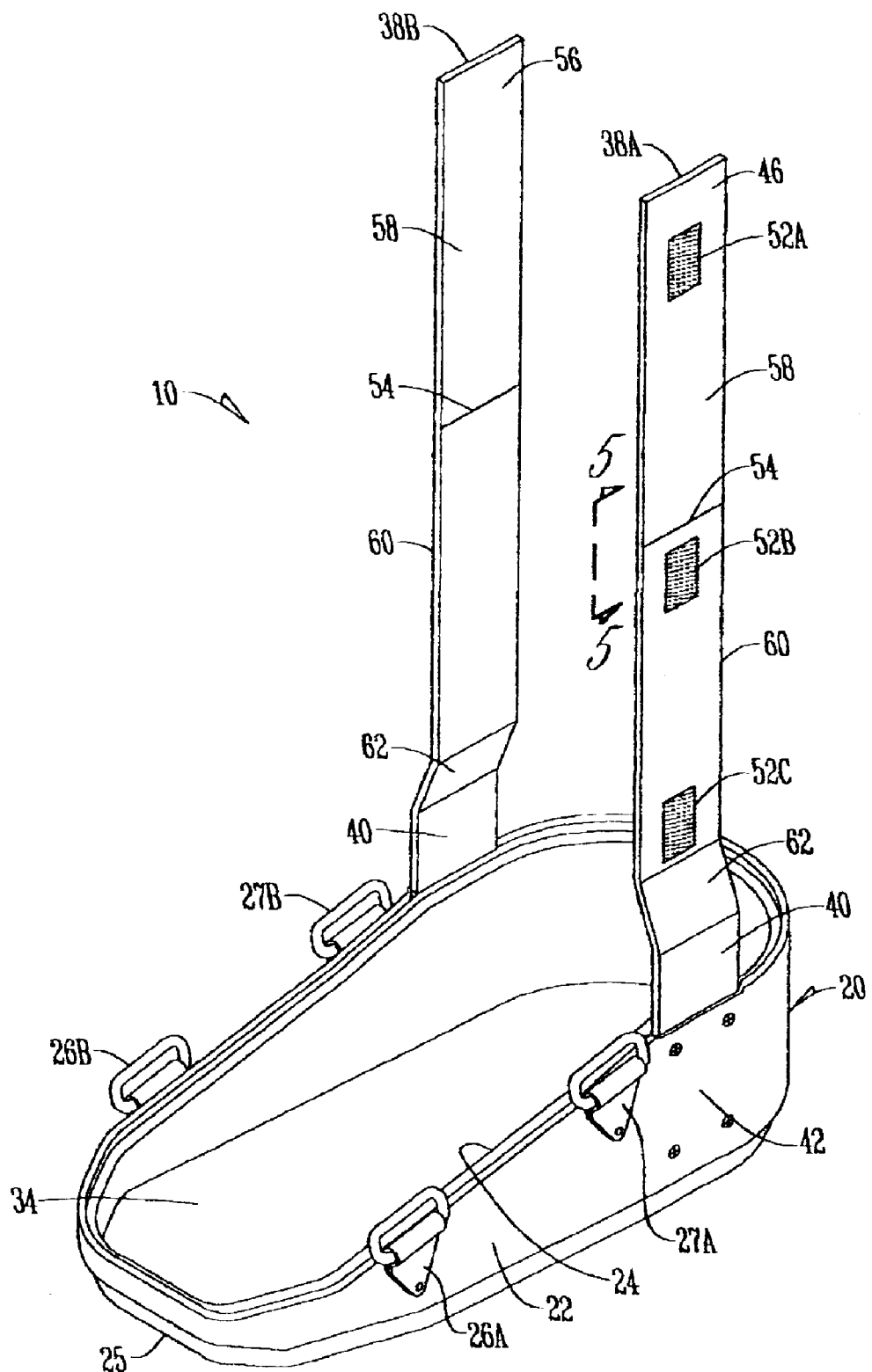
FIG. 1 is a perspective view of the ankle fracture brace of this invention.

With reference to FIGS. 1 and 2, a convertible leg support portion 36 receives a leg 12 of the patient. The leg support portion 36 includes a pair of spaced vertical arms 38A–B each connected by arm lower ends 40 to sides 42 of the main boot body 22 so as to extend upwardly past sides of an ankle 16 of a patient and terminate adjacent sides of a calf 18 of a patient.

Upper end and lower end straps 44 and 45 secure the leg support portion 36 to the leg 12 of the patient. The upper end strap 44 is positioned around the calf 18 of a patient and is connected to the outer surface 46 of vertical arms 38A–B which faces away from the leg 12 of a patient. The lower end strap 45 is positioned adjacent the ankle 16 of a patient and is connected to the outer surface 46 of vertical arms 38A–B.

An ankle strap 47 provides an additional fastener for securing leg support portion 36 to the leg 12 of the patient. The ankle strap 47 is positioned around the ankle 16 of a patient and is connected to the outer surface 46 of vertical arms 38A–B.

Each of the straps 44, 45, and 47 has a fixed loop end 48 permanently secured about a buckle 49. Hook patches 50 are attached to each loose end 51 opposite of the fixed loop ends 48. Each of the straps 44, 45, and 47 are comprised of loop material which is adapted to be detachably secured to the hook patches 50 of loose end 51. Each loose end 51 is treaded through respective buckles 49, and the hook patches 50 are detachably secured to the loop material of straps 44, 45, and 47. Thus, each of the straps 44, 45, and 47 are removably secured around the vertical arms 38A–B, once the hook patches 50 are detachably secured to the loop material of the straps 44, 45, and 47.

Three pair of hook patches 52A–C (only one patch of each pair 52A–C is depicted) are attached to the outer surface 47 of vertical arms 38A–B. The loop material of the straps 44, 45, and 47 is detachably secured to the hook patches 52A–C to affix the straps 44, 45, and 47 to the outer surface 48 of vertical arms 38A–B. One pair of hook patches 52A connects the upper end strap 44 to the vertical arms 38A–B, another pair of hook patches 52B connects the lower end strap 46 to the vertical arms 38A–B, and the last pair of hook patches 52C connects the ankle strap 50 to the vertical arms 38A–B.

Figure 4:
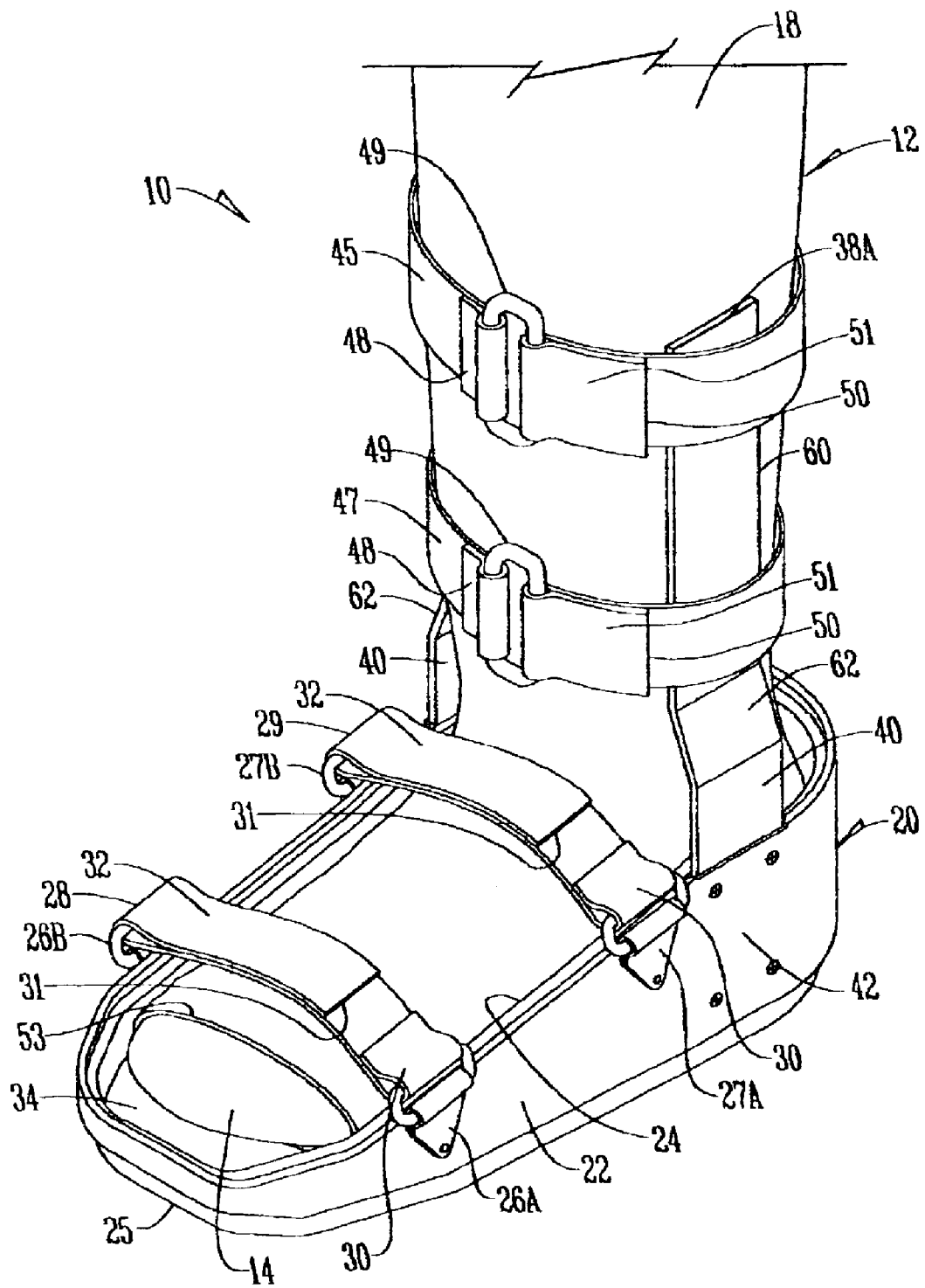
FIG. 4 is a perspective view of the ankle fracture brace of this invention similar to FIG. 3, showing the brace with shortened vertical arms secured to a patients leg.

With reference to FIGS. 2 and 4, a leg liner 53 is provided for covering the leg 12 of a patient. The leg liner 53 separates the leg 12 from the straps 28, 29, 44, 45, and 47 as well as vertical arms 38A–B. This separation allows the leg liner 53 to prevent undesirable friction between the leg 12 of a patient and the ankle fracture brace 10 of the invention.

Figure 5:
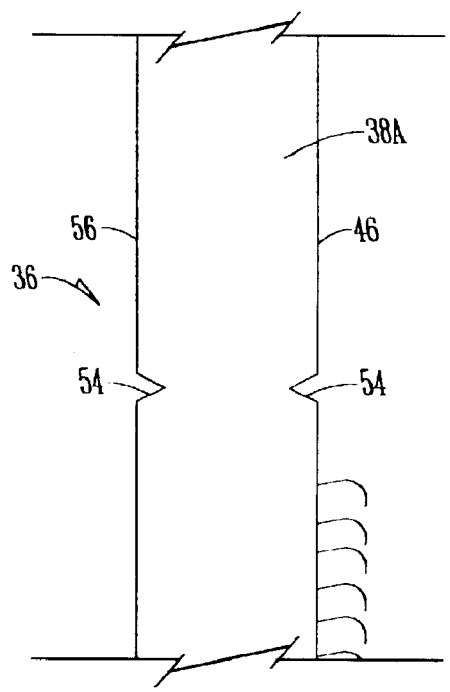
FIG. 5 is an end view of a vertical arm of the ankle fracture brace of this invention taken along line 5—5 of FIG. 1.
Figure 6:
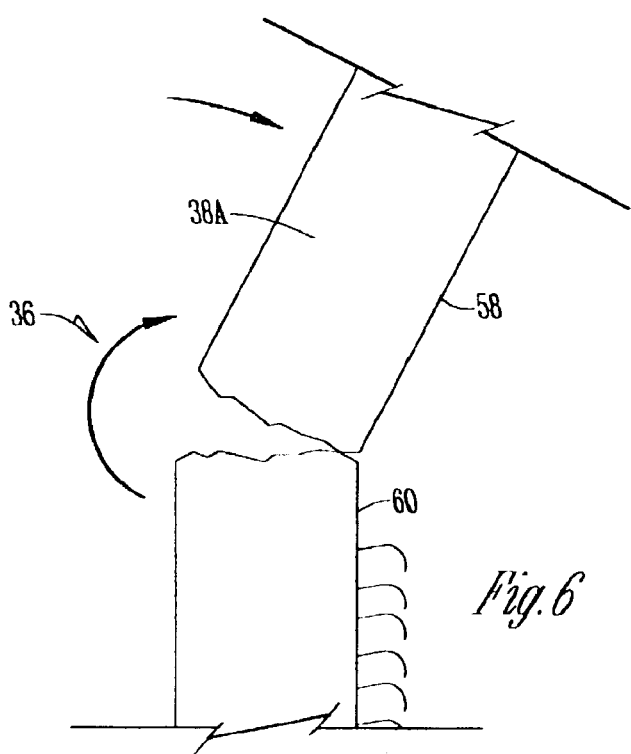
FIG. 6 is an end view of the vertical arm of FIG. 5, showing the breakage of the vertical arm along a horizontal break line.

With reference to FIGS. 1, 5 and 6, a horizontal break line 54 is formed on opposite sides of each of the arms 38A–B between the upper end and lower end straps 44 and 45. The horizontal break lines 54 are formed as a depression in the arms 38A–B creating a breakable area of weakness in the arms 38A–B. As indicated, the horizontal break lines 54 are located on both the outer surface 47 of vertical arms 38A–B as well as an inner surface 56 of vertical arms 38A–B which faces towards the leg 12 of a patient.

Figure 3:
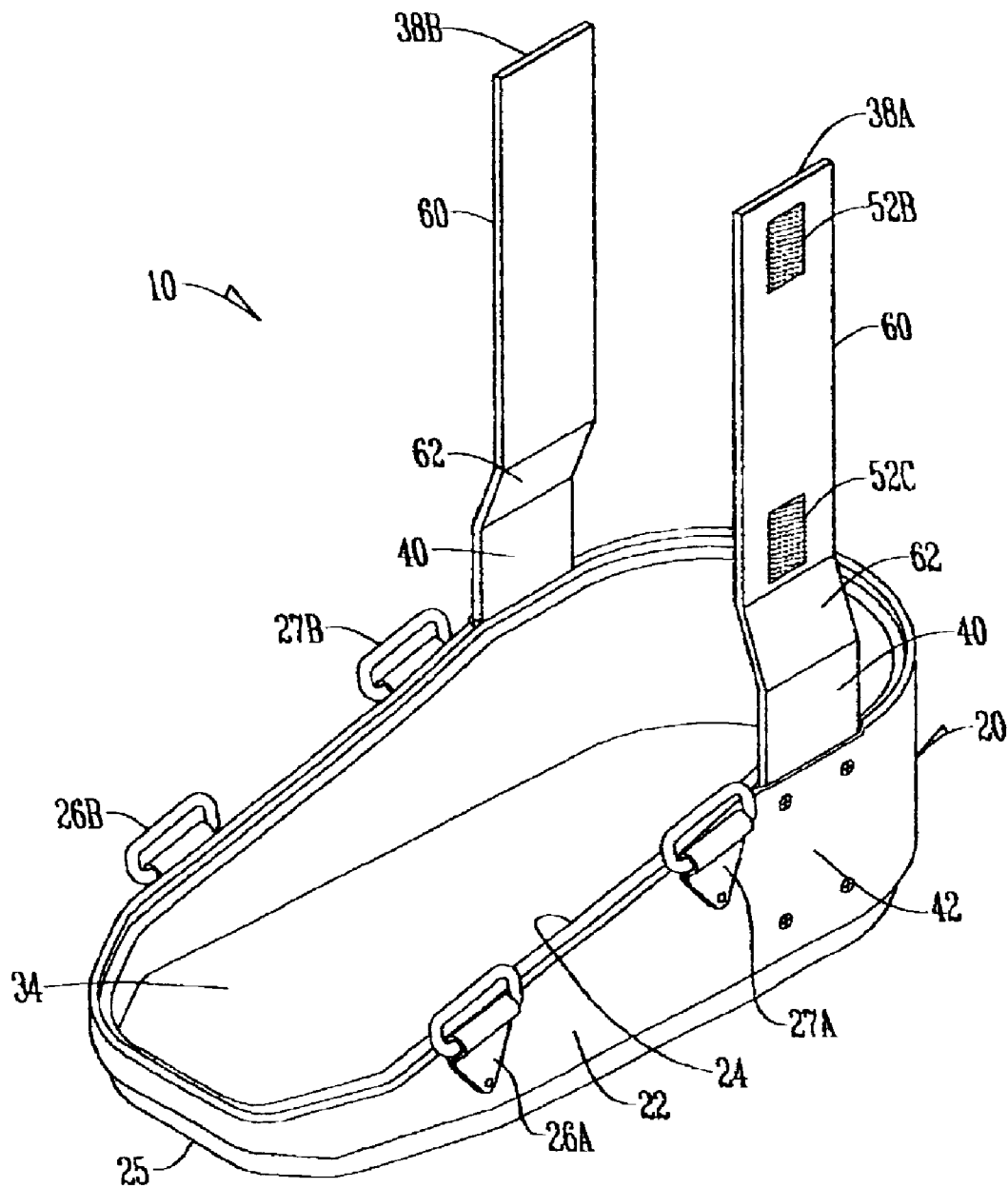
FIG. 3 is a perspective view of the ankle fracture brace of this invention, showing the brace with shortened vertical arms.

The horizontal break lines 54 permit a user to selectively sever the vertical arms 38A–B on the-break lines 54 into an arm upper end 58 and an arm lower end 60. This is done by manually bending, for example, the upper ends of the arms in a lateral direction as shown in FIG. 6. Once the vertical arms 38A–B are broken, the upper end 58 may be removed. The remaining portion of the ankle fracture brace 10 forms a low profile ankle fracture brace as shown in FIGS. 3 and 4. The potential to remove the upper ends 58 of the vertical arms 38A–B permits a user to alter the height of the ankle fracture brace 10. This height alteration of the ankle fracture brace 10 permits the present invention to accommodate separate patient uses of the ankle brace 10.

With reference to FIG. 1, the arm lower ends 60 each have an ankle bend 62 therein. The ankle bend 62 is positioned to fit about the ankle 16 of a patient to provide a greater distance between the vertical arms 38A–B near the ankle 16, as compared to the distance between the vertical arms 38A–B near the calf 18 of a patient.

The break lines 54 on opposite sides of the arms facilitate the breaking action and leaves less of a burr at the break lines 54 after the breakage has taken place.

It is therefore seen that this device provides an ankle fracture brace with a leg support portion which can be easily changed to a second height for a separate use.

It is therefore seen that this device will achieve all of its stated objectives.

What is claimed is:

1. An ankle fracture brace for immobilization and rehabilitation of the foot and ankle, comprising:

a foot support portion adapted to receive a foot of a patient;

a leg support portion adapted to receive a leg of the patient, the leg support portion including a pair of spaced vertical arms connected by arm lower ends to sides of the foot support portion so as to extend upwardly past sides of an ankle of a patient and terminating adjacent sides of a calf of a patient;

upper end and lower end straps for securing the leg support portion to the leg of the patient, being connectable to the vertical arms adjacent the calf and ankle, respectively; and a horizontal break line in each of the arms between the upper end and lower end straps for selectively severing the arms on the break lines to accommodate different patient uses of the ankle brace.

2. The device of claim 1 wherein laterally spaced horizontal break lines are located in each of the arms on both inner and outer surfaces thereof.

3. The device of claim 2 wherein the break lines on each arm dwell in the same horizontal place.

4. The device of claim 1 wherein the foot support portion has a main boot body with an upper opening therein for receiving the foot, a pair of strap holders are connected to the main boot body on opposite sides of the upper opening, and a foot strap adapted to secure the foot within the main boot body is removably secured between these strap holders.

5. The device of claim 1 wherein lower ends of the arms have an ankle bend therein providing a greater distance between the vertical arms near the ankle of a patient, as compared to the distance between the vertical arms near the leg of a patient.

6. The device of claim 1 wherein the vertical arms include pairs of hook patches formed of male micro hook fabric, one pair of hook patches connects the upper end strap to the vertical arms adjacent the calf and another pair of hook patches connects the lower end strap to the vertical arms adjacent the ankle.

\* \* \* \* \*